(12) United States Patent
O'Day (10) Patent No.: US 8,574,218 B2
(45) Date of Patent: Nov. 5, 2013

(54) CATHETER, FLUID CONVEYING METHOD, AND PERCUTANEOUS PROCEDURE

(75) Inventor: Therese O'Day, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 328 days.

(21) Appl. No.: 12/776,650

(22) Filed: May 10, 2010

(65) Prior Publication Data

US 2011/0276022 A1 Nov. 10, 2011

(51) Int. Cl.
*A61M 25/00* (2006.01)
*A61M 1/00* (2006.01)

(52) U.S. Cl.
USPC .......................................... 604/523; 604/27

(58) Field of Classification Search
USPC ........ 604/43, 93.01, 264–266, 541–544, 523, 604/27
See application file for complete search history.

(56) References Cited

U.S. PATENT DOCUMENTS

| | | | |
|---|---|---|---|
| 4,650,463 A * | 3/1987 | LeVeen et al. ................... | 604/43 |
| 4,717,379 A * | 1/1988 | Ekholmer ....................... | 604/43 |
| 4,968,307 A | 11/1990 | Dake et al. | |
| 4,995,872 A | 2/1991 | Ferrara | |
| 5,100,383 A | 3/1992 | Lichtenstein | |
| 5,160,325 A | 11/1992 | Nichols et al. | |
| 5,267,979 A | 12/1993 | Appling et al. | |
| 5,405,334 A | 4/1995 | Roth et al. | |
| 5,425,723 A | 6/1995 | Wang | |
| 5,533,986 A | 7/1996 | Mottola et al. | |
| 5,554,114 A | 9/1996 | Wallace et al. | |
| 5,569,215 A | 10/1996 | Crocker | |
| 5,573,520 A | 11/1996 | Schwartz et al. | |
| 5,609,574 A | 3/1997 | Kaplan et al. | |
| 5,647,859 A | 7/1997 | Lampropoulos et al. | |
| 5,665,076 A | 9/1997 | Roth et al. | |
| 5,713,853 A | 2/1998 | Clark et al. | |
| 5,797,886 A | 8/1998 | Roth et al. | |
| 5,817,072 A | 10/1998 | Lampropoulos et al. | |
| 5,855,563 A | 1/1999 | Kaplan et al. | |

(Continued)

FOREIGN PATENT DOCUMENTS

| | | |
|---|---|---|
| FR | 2248057 | 10/1973 |
| FR | 2248057 | 5/1975 |
| FR | 2940914 | 7/2010 |
| WO | 93/08864 | 5/1993 |

OTHER PUBLICATIONS

Poulsen, Mottola, Stocker; An In Vitro Comparison of Thrombolytic Infusion Catheters; 1998; pp. 1-8; Merit Medical Systems, Inc.; South Jordan, Utah, U.S.

*Primary Examiner* — Matthew F Desanto
(74) *Attorney, Agent, or Firm* — Liell & McNeil (57) ABSTRACT

A catheter includes an elongate catheter body having an outer surface with a non-uniform contour and including a plurality of maximum surface elevation points and a plurality of minimum surface elevation points defining a non-uniform elevation profile relative to a longitudinal axis of the catheter body. The outer surface further includes a fluid transfer interface which includes the plurality of minimum surface elevation points and a plurality of porous surface areas, and a tissue contact interface which includes the plurality of maximum surface elevation points and a plurality of nonporous surface areas. The tissue contact interface inhibits external occlusion of the fluid transfer interface during transferring fluid between a fluid lumen defined by the elongate catheter body, and an intraluminal space such as an intravascular space within a patient.

10 Claims, 3 Drawing Sheets

(56) References Cited

U.S. PATENT DOCUMENTS

| | | |
|---|---|---|
| 5,904,670 A | 5/1999 | Schreiner |
| 6,117,125 A | 9/2000 | Rothbarth et al. |
| 6,179,342 B1 | 1/2001 | Shen |
| 6,551,300 B1 | 4/2003 | McGaffigan |
| 6,884,233 B2 * | 4/2005 | Dance et al. .............. 604/101.03 |
| 2004/0249360 A1 * | 12/2004 | Spehalski ...................... 604/523 |
| 2006/0229573 A1 | 10/2006 | Lamborne |
| 2006/0253101 A1 | 11/2006 | Hartlep et al. |
| 2007/0208300 A1 | 9/2007 | Pravong et al. |
| 2007/0213671 A1 | 9/2007 | Hiatt |
| 2010/0280494 A1 | 11/2010 | Matsuura et al. |

* cited by examiner

CATHETER, FLUID CONVEYING METHOD, AND PERCUTANEOUS PROCEDURE

TECHNICAL FIELD

The present disclosure relates generally to catheters, and relates more particularly to contacting an intraluminal surface with a tissue contact interface of a catheter to inhibit external occlusion of a fluid transfer interface during transferring fluid between the catheter and an intraluminal space.

BACKGROUND

Percutaneous access to the cardiovascular system is used to diagnose, evaluate, and treat a variety of conditions. A typical procedure involves passing a wire guide through an opening in a patient's skin to a vascular structure such as a vein or artery. The wire guide can then be passed through the cardiovascular system to a location of interest within the patient. Once the wire guide has been appropriately positioned, a catheter may be guided by the wire guide to a location where a procedure is to be performed. Angioplasty, imaging, and the placement of stents, grafts, filters and other devices, are common procedures which are performed according to variations of the above general technique. It is also common to use percutaneous access for the placement of catheters which deliver fluid at an intraluminal treatment site. Devices known as infusion catheters are commonly used to deliver a therapeutic treatment fluid such as a thrombolytic agent to a clot or other undesired tissue within a vein or artery. A wide variety of infusion catheter designs are known and commercially available. One general class of infusion catheters utilizes a longitudinally extending lumen which connects a supply of therapeutic fluid located outside of the patient with an intraluminal space by way of ports communicating between the lumen and the intraluminal space.

A typical infusion procedure involves leaving an infusion catheter within a patient for a period of time while treatment fluid flows from the fluid supply into the infusion catheter, and thenceforth into the intraluminal space. A variety of factors can influence how long the infusion procedure lasts. The size of the vascular structure which includes the treatment site, the type of treatment fluid such as a type of lytic agent, geometry and/or age of a clot or other intravascular material, and still other factors such as the distance fluid must travel from the fluid supply to the treatment site, can all affect the selection and administration of a particular infusion procedure. Decisions regarding the selection and administration of a particular infusion procedure are generally made by the attending clinician, and may be updated as the procedure progresses. In any event, there can be a relatively wide range in infusion procedure duration, volume of fluid infused, infusion technique such as pulsed or continuous flow and the particular type of infusion catheter used. In some instances fluid may be infused, often at a relatively high infusion pressure, for a relatively short period of time, for example less than one hour. In other cases, the total infusion time may be five, six or even twelve hours or greater, and infusion may take place intermittently or more or less continuously at a range of different infusion pressures, from relatively low to relatively high.

While various practices have been successful for years, there remains room for improvement. Basic assumptions exist about the operation and behavior of infusion catheters while resident in a vein or artery. For example, it is often assumed that all portions of an infusion length of an infusion catheter will predictably, reliably and uniformly infuse fluid into an intraluminal treatment site throughout the entire course of an infusion procedure. These basic assumptions may not always be valid, however, particularly for procedures using relatively low infusion pressures and prolonged residency of an infusion catheter in a vein or artery.

SUMMARY OF THE INVENTION

In one aspect, an elongate catheter body defines a longitudinal axis extending between a proximal catheter end and a distal catheter end, the elongate catheter body further including an inner surface defining a fluid lumen opening at the proximal catheter end, and an outer surface. The outer surface includes a non-uniform contour relative to the longitudinal axis. The outer surface further includes a plurality of maximum surface elevation points and a plurality of minimum surface elevation points defining a non-uniform elevation profile, and a plurality of porous surface areas and a plurality of nonporous surface areas defining a non-uniform porosity profile. The outer surface further includes a fluid transfer interface which includes the plurality of minimum surface elevation points and the plurality of porous surface areas for transferring a fluid between the fluid lumen and an intraluminal space, and a tissue contact interface which includes the plurality of maximum surface elevation points and the plurality of nonporous surface areas for inhibiting external occlusion of the fluid transfer interface during transferring the fluid.

In another aspect, a method of conveying a fluid between an extraluminal space and an intraluminal space includes fluidly connecting a fluid lumen of a catheter with an intraluminal space having a fluid therein by way of a porous fluid transfer interface which includes a plurality of minimum surface elevation points of an outer surface of the catheter. The method further includes inhibiting external occlusion of the fluid transfer interface at least in part by contacting an intraluminal surface with a nonporous tissue contact interface which includes a plurality of maximum surface elevation points of the outer surface of the catheter. The method still further includes transferring a second fluid between the extraluminal space and the intraluminal space at least in part by infusing the second fluid from the fluid lumen into the intraluminal space.

In still another aspect, a method of performing a percutaneous procedure on a patient includes fluidly connecting a fluid lumen of a catheter with an intraluminal space within the patient by way of a porous fluid transfer interface including a plurality of minimum surface elevation points of an outer surface of the catheter. The method further includes contacting an intraluminal surface within the patient at a plurality of contact locations with a nonporous tissue contact interface including a plurality of maximum surface elevation points of the outer surface of the catheter. The method still further includes transferring fluid from the fluid lumen to the intraluminal space by way of the fluid transfer interface.

DETAILED DESCRIPTION

Figure 1:
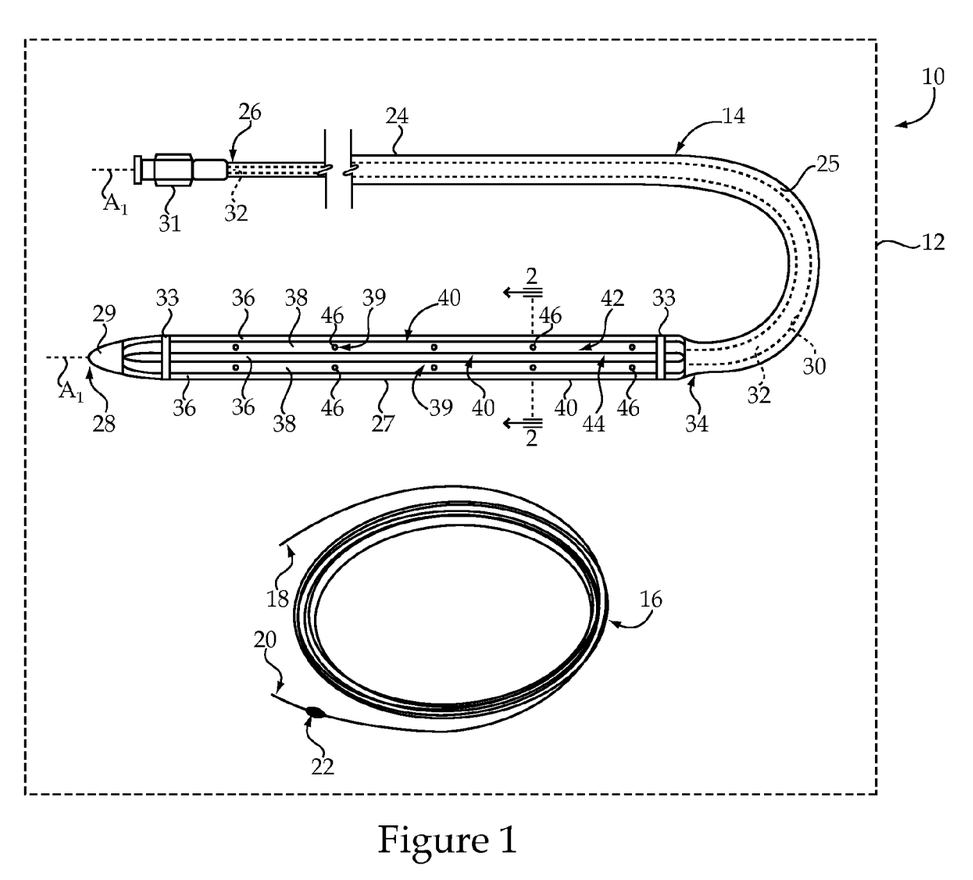
FIG. 1 is a side diagrammatic view of an infusion mechanism having a catheter, according to one embodiment.

Referring to FIG. 1, there is shown an infusion mechanism 10 which may be used for treating an intraluminal site in a patient. Infusion mechanism 10 may include a catheter 14, and a wire guide 16, the catheter 14 and wire guide 16 being positioned within a sterile package 12. Sterile package 12 may include a sealed, peel-open pouch in one embodiment, and other packaging features such as a tube protector coil might be included but are omitted from FIG. 1. As will be further apparent from the following description, infusion mechanism 10 is adapted to address certain challenges such as undesired blocking or restriction of a flow of infusion fluid during use.

Wire guide 16 may include a proximal wire guide end 18 and a distal wire guide end 20. A bulb 22 may be positioned on or adjacent to distal wire guide end 20. In one practical implementation strategy, catheter 14 may be configured for over the wire placement at an intraluminal treatment site in a patient. In such an embodiment, catheter 14 may be slid in a proximal to distal direction over wire guide 16 to a location of interest within a patient. In other embodiments, catheter 14 might be placed by way of another strategy such as by passing catheter 14 through a placement sheath or the like positioned within a patient, and then removing or repositioning the placement sheath to allow the use of catheter 14 in a desired manner. Rapid exchange versions of catheter 14, where a wire guide passes through a relatively short portion of a length of catheter 14, are also contemplated.

Catheter 14 may include an elongate catheter body 24 defining a longitudinal axis $A_1$ extending between a proximal catheter end 26 and a distal catheter end 28 which includes a distal catheter tip 29. Elongate body 24 may further include an inner surface 30 defining a fluid lumen 32 opening at proximal catheter end 26, and an outer surface 34. Outer surface 34 may include a non-uniform contour relative to longitudinal axis $A_1$. Outer surface 34 may also include a plurality of maximum surface elevation points 36 and a plurality of minimum surface elevation points 38 defining a non-uniform elevation profile. The respective surface elevation points may be understood as points within outer surface 34 and also within a plane tangent to a curve defined by outer surface 34, as further described herein. Outer surface 34 may further include a plurality of porous surface areas 39 and a plurality of non-porous surface areas 40, defining a longitudinally and/or radially non-uniform porosity profile. Maximum surface elevation points 36 and minimum surface elevation points 38 may also be understood as points within outer surface 34 which are, respectively, at a maximum distance in a radial direction from longitudinal axis $A_1$ and at a minimum distance in the radial direction from longitudinal axis $A_1$, the significance of which will be apparent from the following description.

Outer surface 34 may further include a fluid transfer interface 42 which includes minimum surface elevation points 38 and porous surface areas 39. Elongate catheter body 24 may also include a tissue contact interface 44 which includes maximum surface elevation points 36 and nonporous surface areas 40. Fluid transfer interface 42 and tissue contact interface 44 may thus be understood to include material of catheter body 24. A hole or port would not in and of itself be understood to be a fluid transfer interface. Rather, it might be the material of the catheter body surrounding the hole or port which could include minimum surface elevation points, and be considered porous, by virtue of the hole or port. Porous surface areas 39 and nonporous surface areas 40 may further be understood as portions of outer surface 34 having differing relative permeability to a fluid such as an infusion liquid. Fluid transfer interface 42 may be configured for transferring a fluid such as a thrombolytic fluid between fluid lumen 32 and an intraluminal space. Tissue contact interface 44 may be configured for inhibiting external occlusion of fluid transfer interface 42 during transferring fluid between fluid lumen 32 and an intraluminal space. As further described herein, tissue contact interface 44 may contact tissue within a patient such as clot tissue, fatty deposits, normal vascular tissue, or other tissues, to prevent such tissues from contacting and occluding fluid transfer interface 42 when catheter 14 is in use. In one embodiment, fluid transfer interface 42 may include a discontinuous interface having a plurality of separate fluid transfer regions. A fluid permeable body wall or membrane extending an entirety of an infusion length of a catheter would not comprise a discontinuous interface. Tissue contact interface 44 may also include a discontinuous interface having a plurality of separate tissue contact regions in an alternating arrangement with the plurality of separate fluid transfer regions, as further described herein. Another way to understand such an embodiment is that porous areas may alternate with nonporous areas, and minimum elevation areas may alternate with maximum elevation areas, the respectively alternating characteristics being generally in phase with one another.

In the illustrated embodiment, fluid transfer interface 42 and tissue contact interface 44 are located in a distal catheter segment 27 which includes distal catheter end 28 and distal tip 29. A proximal catheter segment 25 extends proximally from distal catheter segment 27 and includes proximal catheter end 26. It may be noted from FIG. 1 that fluid lumen 32 opens at proximal catheter end 26 such that fluid communication may exist between fluid lumen 32 and a manifold 31 or the like coupled with proximal catheter end 26. Distal catheter segment 27 may include a set of axially spaced radiopaque markers 33 which can indicate, with the assistance of radiography, an approximate location of distal catheter segment 27 within a patient. Inner surface 30 may be fluid impermeable within proximal catheter segment 25, and fluid permeable within distal catheter segment 27 by way of fluid transfer interface 42. Also shown in FIG. 1 are a plurality of effluent ports 46 located within fluid transfer interface 42, and having an axial distribution which defines an infusion length of catheter 14. Markers 33 may be located at opposite ends of the infusion length. Effluent ports 46 may impart fluid permeability to inner surface 30 within distal catheter segment 27. In other embodiments, rather than discrete holes or ports, normally closed slits or even a fluid permeable membrane might be used. While catheter 14 may be designed to have a distal catheter segment which includes an infusion segment, and a separate proximal catheter segment 25 which is not an infusion segment, alternative designs are contemplated wherein an entire length of catheter 14 is used to infuse fluid to an intraluminal space. For example, a catheter might be designed which includes features of distal catheter segment 27 such as a fluid transfer interface and a tissue contact interface which extend a majority or all of a length of the catheter body. Such a device could be coupled with a separate catheter piece having features similar to proximal catheter segment 25, to create a catheter assembly functionally similar to catheter 14.

Figure 2:
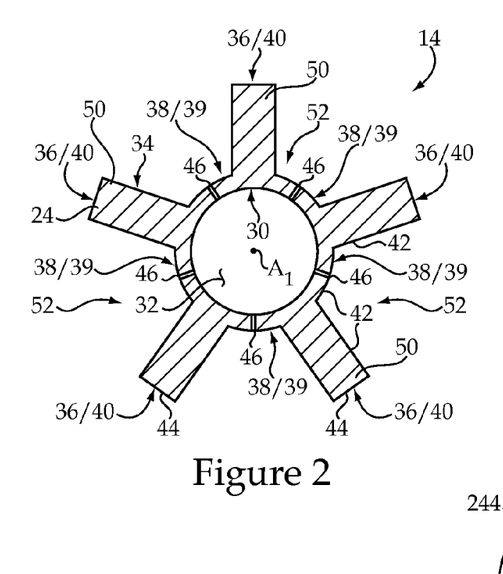
FIG. 2 is a sectioned view taken along line 2-2 of FIG. 1.

Referring to FIG. 2, there is shown a sectioned view through elongate catheter body 24 taken along line 2-2 of FIG. 1. It will be recalled that fluid transfer interface 42 may include a discontinuous interface, and tissue contact interface 44 may also include a discontinuous interface. In FIG. 2, the plurality of different tissue contact regions of tissue contact interface 44 may include a plurality of lobes 50 of outer surface 34. The plurality of fluid transfer regions of fluid transfer interface 42 may include a plurality of grooves 52 in a radially alternating arrangement with lobes 50 and defining a corrugated contour of outer surface 34. In the example embodiment, the corrugated contour includes a radially corrugated contour, where lobes 50 include a plurality of radially spaced lobes each extending along elongate catheter body 24 in an axial direction, for example parallel longitudinal axis $A_1$. Grooves 52 may include a plurality of radially spaced grooves extending in parallel with lobes 50 and in an alternating arrangement therewith. The radially corrugated contour may further include a longitudinally fluted contour defining at least one symmetric shape property, about longitudinal axis $A_1$. The at least one symmetric shape property may include a radially symmetrical shape property exemplified by an approximately radially symmetric star shape of the FIG. 2 embodiment. Effluent ports 46 are shown communicating between outer surface 34 and inner surface 30 to provide fluid communication between fluid lumen 32 and an intraluminal space, as further described herein. As noted above, tissue contact interface 44 may include maximum surface elevation points 36 and nonporous areas 40. Fluid transfer interface 42 may include minimum surface elevation points 38 and porous surface areas 39.

Figure 3:
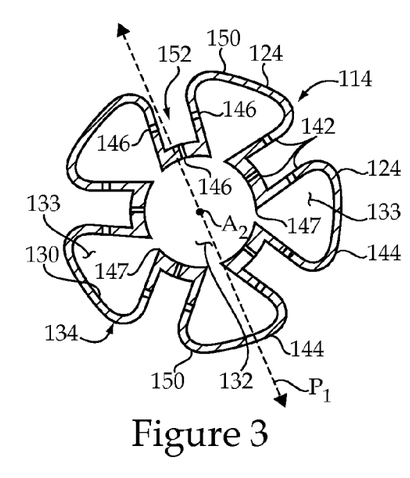
FIG. 3 is a sectioned view of a catheter, according to another embodiment.

Referring now to FIG. 3, there is shown a catheter 114 according to another embodiment in a section plane similar to the section plane shown in FIG. 2 with regard to catheter 14. Catheter 114 includes an elongate catheter body 124 having a fluid lumen 132 extending axially therethrough and defined by an inner surface 130 of catheter body 114. Fluid lumen 132 may include a primary fluid lumen, and inner surface 130 may further define a plurality of secondary lumens 133. Each of lumens 132 and 133 may extend an entirety of an axial infusion length of catheter 14 but need not, and might even have differing axial lengths. A plurality of orifices 147 fluidly connect lumen 132 with lumens 133 and might include elongate slots, for example. A plurality of effluent ports 146 which may include normally open effluent ports are formed in an outer surface 134 of catheter body 114 and fluidly communicate between inner surface 130 and outer surface 134. Similar to catheter 14, outer surface 134 may include a radially corrugated contour, which may also include a longitudinally fluted contour, defined by a plurality of lobes 150 and a plurality of grooves 152. The radially corrugated contour of outer surface 134 may also define a radially symmetric shape property, such as a five petaled cloverleaf shape, about axis $A_2$. A tissue contact interface 144 may include lobes 150, and a fluid transfer interface 142 may include grooves 152. In catheter 114, effluent ports 146 may include ports at a radially inward location approximately at minimum surface elevation points of outer surface 134, and opening within primary lumen 132. Additional effluent ports 146 may be positioned at radially outward locations between minimum surface elevation points and maximum surface elevation points of outer surface 134 and open within secondary lumens 133. This configuration can provide for effluent flow into grooves 152 at multiple radial locations and by way of differing effusion directions.

Figure 4:
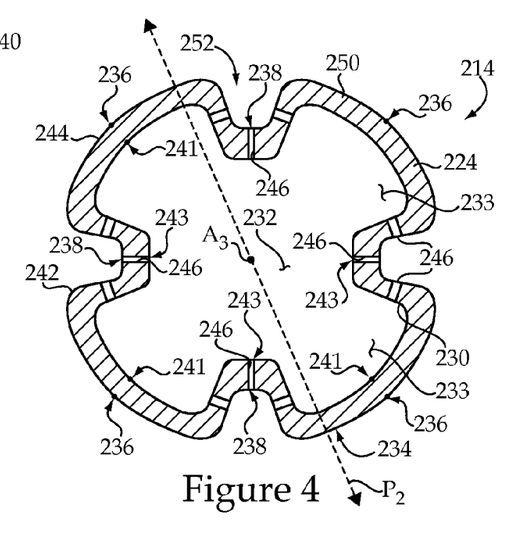
FIG. 4 is a sectioned view of a catheter, according to yet another embodiment.

Turning to FIG. 4, there is shown yet another embodiment of a catheter 214 having an inner surface 230 defining a fluid lumen 232, an outer surface 234, and a plurality of effluent ports 246 fluidly communicating between inner surface 230 and outer surface 234. Fluid lumen 232 may include a primary lumen, and inner surface 230 may define secondary lumens 233. Similar to the previously described embodiments, a tissue contact interface 244 may include a plurality of lobes 250, and a fluid transfer interface 242 may include a plurality of grooves 252. In the FIG. 4 embodiment, lobes 250 comprise a relatively larger proportion of outer surface 234 than that comprised by grooves 252. Tissue contact interface 244 may similarly comprise a relatively larger portion of outer surface 234 than does fluid transfer interface 242. This configuration is different from the embodiment of FIG. 2, for example, having different relative proportions of outer surface 34 comprised by lobes 50 versus grooves 52. Effluent ports 246 are shown approximately at minimum surface elevation points, and also at more radially outward locations.

Catheter 214 may also include a plurality of symmetric shape properties, defined by a non-uniform contour of outer surface 234. In one embodiment, catheter 214 may be radially symmetric about axis $A_3$. Catheter 214 may also be biradially symmetric, meaning that a first half of catheter 214 is a mirror image of a second half of catheter 214 about a plane which includes a plane $P_2$ of axis $A_3$. In the FIG. 3 embodiment, catheter 114 would not be considered biradially symmetric, as halves of catheter 114 are not mirror images about a plane $P_1$ of axis $A_2$. The term "symmetric" should not be understood to mean perfectly symmetric, and is used herein in a manner consistent with that used in botany and zoology to describe forms occurring in nature such as starfish, flowers and the like.

Another geometric attribute of catheter 214, and other embodiments contemplated herein, relates to a relationship between the non-uniform contour defined by outer surface 234, and a non-uniform contour defined by inner surface 230. The non-uniform contour defined by outer surface 234 may define a first non-uniform curve in a plane normal to and intersecting a single point of axis $A_3$. This is the plane of the page in FIG. 4. The first curve may include maximum surface elevation points 236 and minimum surface elevation points 238, and may be understood as following a contour of outer surface 234 for one complete rotation about axis $A_3$. The non-uniform contour defined by inner surface 230 may be analogously understood, and defines a second non-uniform curve which includes maximum surface elevation points 241 of inner surface 230, and minimum surface elevation points 243. The second non-uniform curve may be in phase with the first non-uniform curve. "In phase" means that peaks of the second curve are on average at radial locations relatively closer to radial locations of peaks of the first curve, than to radial locations of valleys of the first curve. Similarly, valleys of the second curve are, on average, relatively closer to valleys of the first curve than to peaks of the first curve. In the FIG. 4 embodiment, the respective curves are exactly, or nearly exactly, in phase, such that maximum surface elevation points 236 (curve peaks) occupy the same radial locations as maximum surface elevation points 241 (curve peaks), and minimum surface elevation points 238 (curve valleys) occupy the same radial locations as minimum surface elevation points 243 (curve valleys). Shaping catheter 214 such that points 236 are, on average, radially closer to points 246, would shift the two curves out of phase. In the FIG. 4 embodiment, the first and second curves define congruent shapes, however, in other embodiments the shapes could be non-congruent, and the first and second curves still considered to be in phase.

It may be noted that no strict distinction is made between what features include a lobe versus what features include a groove. For example, certain portions of lobes 50 in the embodiment of FIG. 2 might be said to be the same as or include certain portions of grooves 52. The intended purpose of the respective features may determine, for example, where a "lobe" ends and a "groove" begins, or whether a given portion of outer surface 34 is part of both a lobe and a groove. Portions of outer surface 34 which have no geometric characteristics of a lobe or groove, such as portions of outer surface 34 within proximal segment 25, would be part of neither a lobe nor a groove. Likewise, portions of outer surface 34 intended for transferring fluid to an intraluminal space would not likely be considered part of a lobe. Portions of outer surface 34 intended to contact an intraluminal surface when catheter 14 is used would likely not be considered part of a groove. Portions of outer surface 34 adjoining a portion intended for contacting an intraluminal surface, and adjoining another portion intended for transferring fluid may be part of both a lobe and a groove. Similar characteristics may be associated with other embodiments contemplated herein.

Each of the embodiments described herein may be made by way of known manufacturing techniques. Elongate catheter bodies 24, 124 and 224 may be formed by way of an extrusion process where an extrusion die is shaped to impart a desired radially non-uniform contour. Effluent ports 46, 146 and 246 may be formed by manually passing a piercing tool or the like through the respective outer surface 34, 134, 234, or some automated process might be used.

Catheters according to the present disclosure may be made from any suitable polymeric material such as nylon or PTFE. No limitation as to the specific dimensions of any catheter encompassed by the present disclosure is intended. Nevertheless, in one embodiment an outer diameter of an elongate catheter body contemplated herein may be in the range of 3 French (FR) to 6 French (FR). The infusion length of catheters contemplated herein can vary widely as well, and may be between 5 centimeters and 60 centimeters, in one embodiment. The overall length of the subject catheter might vary from 40 centimeters to 160 centimeters. In one particular example, any of the embodiments described herein might include a catheter having an outer diameter of 5 FR, an overall catheter length from a terminal proximal catheter end to a terminal distal catheter end of 150 centimeters, and an infusion length between radiopaque markers of 30 centimeters. Arterial infusion rates of 5 cubic centimeters per hour to 20 cubic centimeters per hour, and venous infusion rates of 20 cubic centimeters per hour to 50 cubic centimeters per hour might be used, by way of either continuous infusion flow or pulsed flow, using an infusion pump or some other mechanism. The present disclosure, however, is also not limited in this regard.

INDUSTRIAL APPLICABILITY

Figures 5, 6:
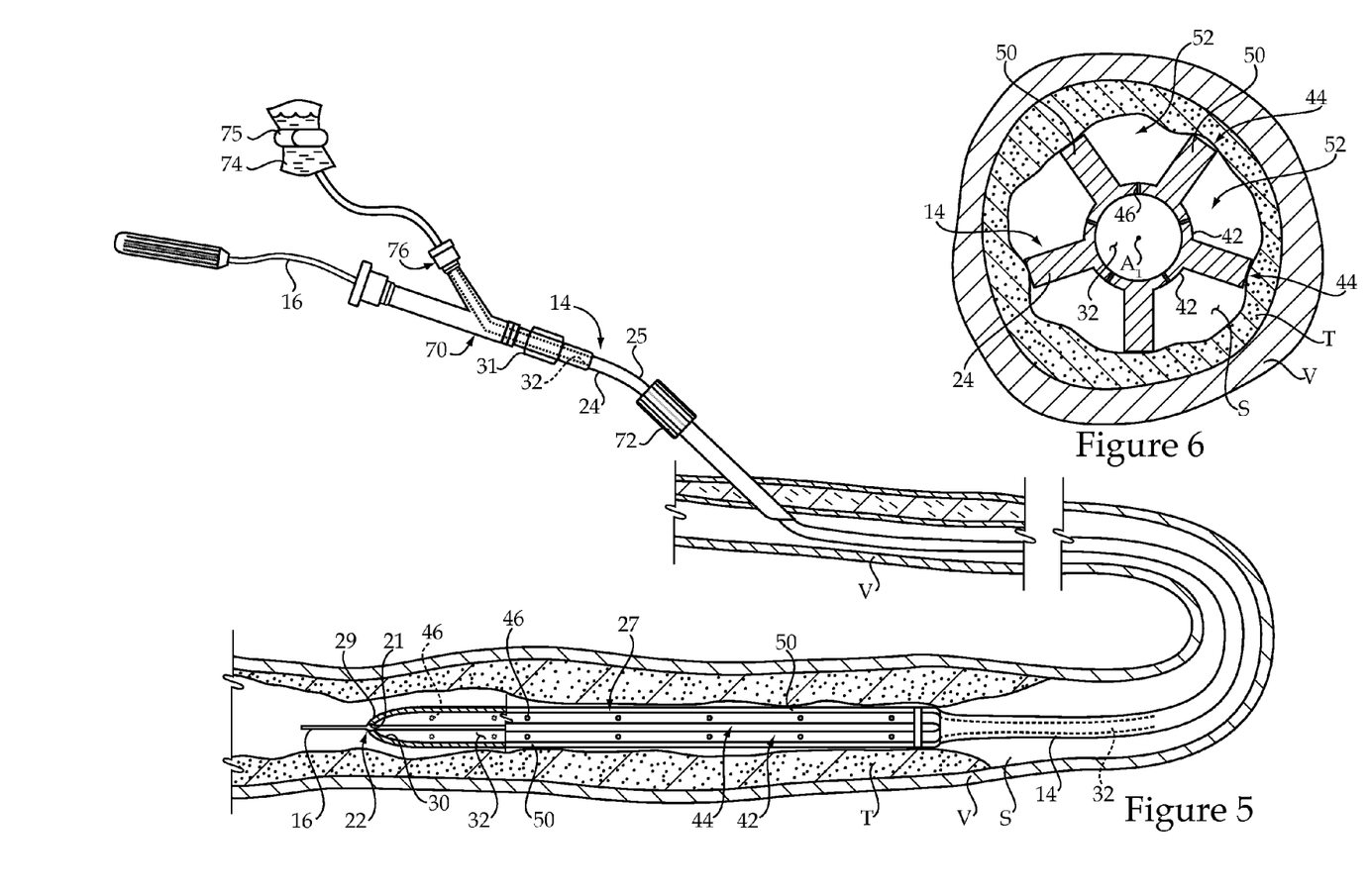
FIG. 5 is a partially sectioned diagrammatic view of an infusion mechanism having a catheter, at one stage of a percutaneous procedure according to one embodiment.
FIG. 6 is a sectioned diagrammatic view of a catheter at the stage of a percutaneous procedure shown in FIG. 6.

Referring to FIG. 5, there is shown catheter 14 as it might appear when used to convey a fluid between an extraluminal space and an intraluminal space S within a body lumen in a patient, such as an intravascular space. In the application depicted in FIG. 6, catheter 14 has been positioned within a vascular structure V of a patient by way of percutaneous entry through an introducer sheath 72. Intraluminal space S may include a space within a portion of vascular structure V where a thrombus T has formed. A fluid, for example blood, will typically reside in intraluminal space S, which may assist in dispersing infusate and also in carrying away bits of broken up or dissolving thrombus material. Wire guide 16 is shown having been positioned within vascular structure V, and catheter 14 has been passed over wire guide 16 to reach the treatment site and seal a distal outlet 21 in distal tip 29 with bulb 22. A Y-fitting 70 is coupled with manifold 31, in turn connected with catheter body 24. A fitting 76 or the like may be used to fluidly connect Y-fitting 70, and thus fluid lumen 32, with an extraluminal fluid supply 74. A pressure cuff 75 or the like may be coupled with fluid supply 74 to supply fluid to catheter 14 at a supply pressure in a conventional manner. An infusion pump, or some other mechanism such as a gravity feed mechanism or even a syringe, might be used to supply fluid to catheter 14.

Positioning catheter 14 approximately as shown in FIG. 5, and connecting with fluid supply 74, and blocking outlet 21 can enable subsequent transferring of fluid between an extraluminal space such as fluid supply 74 and intraluminal space S by way of fluid lumen 32. Fluid lumen 32 may be fluidly connected with intraluminal space S by way of porous fluid transfer interface 42. Establishing fluid connections and positioning catheter 14 as described herein will enable infusing of fluid such as a liquid lytic agent into intraluminal space S at a plurality of fluid transfer locations corresponding to each of the fluid transfer regions of fluid transfer interface 342. While it is contemplated that use as an infusion catheter is one practical implementation strategy, in other embodiments catheter 14 or another catheter having features according to the present disclosure might be used for other purposes.

Similarly, while percutaneous entry into a patient's cardiovascular system by forming an access opening in the patient, passing wire guide 16 through the access opening, and sliding catheter 14 in a proximal to distal direction over wire guide 16 are one example of a suitable access and guiding procedure, the present disclosure is also not limited in this regard. In other embodiments, rather than guiding catheter 14 with wire guide 16, a placement sheath might be used through which catheter 14 is passed. Further still, catheter 14 might be configured as a rapid exchange catheter. In such an embodiment, lumen 32 might be closed near distal tip 29, and a wire guide passed through a relatively short wire guide lumen opening at or near distal tip 29. Where used in procedures other than percutaneous vascular procedures, catheter 14 might be placed by still other methods.

It may further be noted that an intravascular surface which includes a surface of thrombus T is in contact with tissue contact interface 44 in FIG. 5. In particular, lobes 50 contact thrombus T at a plurality of different locations. Contacting thrombus T with tissue contact interface 44 will tend to inhibit contact between fluid transfer interface 42 and thrombus T. In other words, contact of tissue contact interface 44 with thrombus T will tend to prevent thrombus T from contacting and externally occluding fluid transfer interface 42 during infusing fluid. Each of the separate contact regions of tissue contact interface 44 may contact thrombus T, and each of the plurality of fluid transfer regions of fluid transfer interface 342 may be protected from contact with thrombus T and thus each capable of infusing fluid into intraluminal space S. In other instances, less than all of the available tissue contact regions will actually contact tissue within the patient, and some of the separate fluid transfer regions might actually be blocked. The present disclosure is nevertheless contemplated to provide an improved capability to deliver infusion fluid, as at least some of fluid transfer interface 42 will typically always be available, not occluded, for infusing fluid into an intraluminal space. In the case of lower pressure infusion, a tendency for intraluminal tissue to partially or totally block effluent ports of an infusion catheter may be more acute than in higher pressure infusion. While the present disclosure is not limited to any particular infusion duration or pressure, it may be advantageously applied to certain lower pressure, longer duration infusion procedures. Both the lower exit pressure of infusate, and the tendency for the infusion catheter to shift or differently contact tissue over time, or still other factors may be responsible for this superior performance. Once an infusion procedure is completed, catheter 14 and wire guide 16 may be removed in a conventional manner.

Referring to FIG. 6, there is shown catheter 14 in an axial section view as it might appear when used in the procedure shown and described with regard to FIG. 5. It may be noted that tissue contact interface 44 contacts thrombus T within vascular structure V at a plurality of tissue contact locations, spaced radially about axis $A_1$. Fluid transfer interface 42 is not contacted by thrombus T, and is thus available for transferring fluid between fluid lumen 32 and intraluminal space S by way of effluent ports 46. Other embodiments described herein may be used in an analogous manner, but with certain differences. In the case of the embodiments of FIGS. 3 and 4, transferring fluid into an intraluminal space may include transferring the fluid from the primary lumens 132, 232 into the secondary lumens 133, 233, and then into the intraluminal space.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. An infusion catheter comprising:
    an elongate catheter body defining a longitudinal center axis extending between a proximal catheter end and a distal catheter end, and including an inner surface extending circumferentially around the longitudinal center axis and defining an axially extending fluid lumen centered thereon opening at the proximal catheter end, and an outer surface;
    the catheter body further being formed of a material and single-walled, such that an uninterrupted thickness of the material forms the inner and outer surfaces and extends radially between the inner and outer surfaces throughout the catheter body;
    the outer surface having a non-uniform contour relative to the longitudinal center axis, and a plurality of maximum surface elevation points upon a plurality of longitudinally extending lobes, and a plurality of minimum surface elevation points within a plurality of longitudinally extending grooves;
    the outer surface further including a plurality of porous surface areas including a plurality of effluent ports within the plurality of longitudinally extending grooves and being in fluid communication with the fluid lumen, for transferring a fluid from the fluid lumen into the plurality of longitudinally extending grooves for infusion into an intraluminal space in a patient;
    the outer surface further including a plurality of nonporous surface areas located upon the plurality of longitudinally extending lobes, for inhibiting external occlusion during the infusion of the fluid; and
    the plurality of longitudinally extending grooves each tapering from a narrower width at a radially inward location to a greater width at a radially outward location where the fluid exits the groove for infusion, such that the elongate catheter body forms a star shape in axial cross section.

2. The catheter of claim 1 wherein the plurality of porous surface areas are in an alternating arrangement with the plurality of nonporous surface areas.

3. The catheter of claim 2 further comprising a proximal catheter segment and a distal catheter segment, the porous surface areas and the nonporous surface areas being located within the distal catheter segment, and the inner surface being fluid impermeable within the proximal catheter segment, and fluid permeable within the distal catheter segment by way of the porous surface areas.

4. The catheter of claim 3 wherein the plurality of effluent ports having an axial distribution defining a catheter infusion length, and the catheter further including a radiopaque marker positioned adjacent each of a first end and a second end of the catheter infusion length.

5. The catheter of claim 4 wherein the non-uniform contour includes a longitudinally fluted contour defining at least one symmetric shape property of the elongate catheter body, about the longitudinal axis.

6. The catheter of claim 5 wherein the at least one symmetric shape property includes a radially symmetric shape property.

7. The catheter of claim 4 wherein the non-uniform contour includes a radially corrugated contour, and the plurality of lobes including a plurality of radially spaced lobes and the plurality of grooves including a plurality of radially spaced grooves having an alternating arrangement with the plurality of radially spaced lobes.

8. An infusion catheter comprising:
    an elongate catheter body defining a longitudinal axis extending between a proximal catheter end and a distal catheter end, the elongate catheter body further including an inner surface defining a fluid lumen opening at the proximal catheter end, and an outer surface;
    the outer surface having a non-uniform contour relative to the longitudinal center axis and including a plurality of maximum surface elevation points and a plurality of minimum surface elevation points defining a non-uniform elevation profile, the outer surface further including a plurality of porous surface areas in fluid communication with the fluid lumen and a plurality of nonporous surface areas defining a non-uniform porosity profile; and
    the outer surface further having a fluid transfer interface which includes the plurality of minimum surface elevation points and the plurality of porous surface areas, for transferring a fluid from the fluid lumen into an intraluminal space in a patient, and a tissue contact interface which includes the plurality of maximum surface elevation points and the plurality of nonporous surface areas, for inhibiting external occlusion of the fluid transfer interface during transferring the fluid;
    the fluid transfer interface including a discontinuous interface having a plurality of separate fluid transfer regions, and the tissue contact interface including a discontinuous interface having a plurality of separate tissue contact regions in an alternating arrangement with the plurality of separate fluid transfer regions;
    the catheter further having a proximal catheter segment and a distal catheter segment, the fluid transfer interface and the tissue contact interface being located within the distal catheter segment, and the inner surface being fluid impermeable within the proximal catheter segment, and fluid permeable within the distal catheter segment by way of the fluid transfer interface;

wherein the outer surface further includes a plurality of normally open effluent ports located within each of the plurality of fluid transfer regions and communicating between the inner and outer surfaces, and wherein the fluid lumen includes a central primary lumen and the inner surface further defines a plurality of radially outward secondary lumens fluidly connected with the primary lumen; and wherein the plurality of fluid transfer regions and corresponding effluent ports are within a plurality of grooves formed in the elongate catheter body, and the plurality of effluent ports includes a first set of effluent ports within each groove opening within one of the plurality of secondary lumens, and a second set of effluent ports within each groove opening within the primary lumen, and wherein each of the grooves tapers from a narrower width at a radially inward location where the fluid is transferred into the groove from the corresponding first set of effluent ports to a greater width at a radially outward location where the fluid exits the groove for infusion.

9. The catheter of claim 8 wherein:

the non-uniform contour defines a first curve in a plane normal to and intersecting a single point of the longitudinal axis, the first curve including the plurality of maximum surface elevation points and the plurality of minimum surfaces elevation points; and the inner surface includes a second non-uniform contour defining a second curve in the plane, the second curve including a plurality of maximum surface elevation points and a plurality of minimum surface elevation points of the inner surface, and the second curve being in phase with the first curve.

10. An infusion catheter comprising:

an elongate catheter body defining a longitudinal axis extending between a proximal catheter end and a distal catheter end, the elongate catheter body further including an inner surface defining a fluid lumen opening at the proximal catheter end, and an outer surface;

the outer surface having a non-uniform contour relative to the longitudinal center axis and including a plurality of maximum surface elevation points and a plurality of minimum surface elevation points defining a non-uniform elevation profile, the outer surface further including a plurality of porous surface areas in fluid communication with the fluid lumen and a plurality of nonporous surface areas defining a non-uniform porosity profile;

the outer surface further having a fluid transfer interface which includes the plurality of minimum surface elevation points and the plurality of porous surface areas, for transferring a fluid from the fluid lumen into an intraluminal space in a patient, and a tissue contact interface which includes the plurality of maximum surface elevation points and the plurality of nonporous surface areas, for inhibiting external occlusion of the fluid transfer interface during transferring the fluid;

the fluid transfer interface including a plurality of normally open effluent ports communicating between the inner and outer surfaces and positioned within a plurality of grooves formed in the elongate catheter body;

the fluid lumen includes a central primary lumen and the inner surface further defines a plurality of radially outward secondary lumens fluidly connected with the primary lumen;

the plurality of effluent ports includes a first set of effluent ports within each groove and opening within one of the plurality of secondary lumens, and a second set of effluent ports within each groove and opening within the primary lumen; and each of the grooves tapers from a narrower width at a radially inward location where the fluid is transferred into the groove from the corresponding first set of effluent ports to a greater width at a radially outward location where the fluid exits the groove for infusion.

* * * * *